(12) United States Patent
Su

(10) Patent No.: US 12,616,610 B1
(45) Date of Patent: May 5, 2026

(54) EYE MASK

(71) Applicant: Jiyan Su, Puning (CN)

(72) Inventor: Jiyan Su, Puning (CN)

( * ) Notice: Subject to any disclaimer, the term of this patent is extended or adjusted under 35 U.S.C. 154(b) by 7 days.

(21) Appl. No.: 19/082,763

(22) Filed: Mar. 18, 2025

(51) Int. Cl.
   *A61F 9/04* (2006.01)
   *A61M 21/00* (2006.01)
   *A61M 21/02* (2006.01)
(52) U.S. Cl.
   CPC .............. *A61F 9/04* (2013.01); *A61M 21/02* (2013.01); *A61M 2021/0027* (2013.01)
(58) Field of Classification Search
   CPC .. A61F 9/04; A61M 2021/0027; A61M 21/02
   USPC .................................................... 2/15
   See application file for complete search history.

(56) References Cited

U.S. PATENT DOCUMENTS

| | | | | |
|---|---|---|---|---|
| 5,903,395 A | * | 5/1999 | Rallison .............. | G02B 27/0172 359/630 |
| D1,024,616 S | * | 4/2024 | Liao ................................ | D6/601 |
| 2003/0014096 A1 | * | 1/2003 | Burkhart ................... | A61F 9/04 607/109 |

| | | | | |
|---|---|---|---|---|
| 2021/0015671 A1 | * | 1/2021 | Seidenfeld ............ | A61M 21/00 |
| 2021/0375253 A1 | * | 12/2021 | Turner-Fernback ......................... H04R 1/1083 | |
| 2022/0087867 A1 | * | 3/2022 | Bamberg ................... | A61F 9/04 |
| 2024/0036306 A1 | * | 2/2024 | Jin ...................... | G02B 27/0172 |

FOREIGN PATENT DOCUMENTS

CN          222265530 U    * 12/2024

OTHER PUBLICATIONS

CN-222265530-U—Google Tranlation—Zhong—Dec. 31, 2024.*
CN-222265530 (Year: 2024).*

* cited by examiner

*Primary Examiner* — Alissa J Tompkins
*Assistant Examiner* — Catherine M Ferreira
(74) *Attorney, Agent, or Firm* — HOWARD M COHN and Associates, LLC

(57) ABSTRACT

An eye mask is provided, including a main body and loudspeakers. The main body is configured to worn on a human head, and a temperature variable substance is disposed in the main body. The loudspeakers are disposed in the main body, at least one of the loudspeakers is disposed at each of two opposite sides of the main body, each of the loudspeakers is configured to play audio toward a human ear. Functionality of the eye mask is enhanced and diversified. Both comfort and functionality of the eye mask is enhanced.

19 Claims, 3 Drawing Sheets

EYE MASK

TECHNICAL FIELD

The present disclosure relates to a technical field of wearable devices, and in particular to an eye mask.

BACKGROUND

In modern life, optimal sleep quality is crucial for maintaining physical and mental health of humans. However, due to environmental factors, work-related stress, and prevalent use of electronic devices, an increasing number of people suffer from sleep disorders and eye strain. To address these issues, eye masks are widely adopted as auxiliary tools to improve sleep quality and alleviate ocular discomfort. Nevertheless, conventional eye masks are typically constructed from lightweight materials primarily designed to block light, yet they often fail to provide a close fit with human eye contours, resulting in inadequate soothing effects. Furthermore, the conventional eye masks are single in function and struggle to meet growing demands of users for comfort and functionality.

SUMMARY

Embodiments of the present disclosure provide an eye mask designed to enhance both comfort and functionality.

The embodiments of the present disclosure provide the eye mask, including a mask body and at least one loudspeaker. The main body is configured to be worn on a human body and cover eyes of the human body, and a weighted portion is disposed in the mask body. The at least one loudspeaker is disposed in the mask body and is configured to offset from the eyes of the human body.

Furthermore, the mask body includes a covering portion and a connecting portion, the covering portion defines an accommodating space, the weighted portion and the at least one loudspeaker are disposed in the accommodating space, the connecting portion is connected to two sides of the covering portion and cooperates with the covering portion to be worn on the human body.

Furthermore, the covering portion includes a central area and two side areas, the two side areas are configured to respectively cover different ears of the human body, and the central area is disposed between the two side areas. Two loudspeakers are provided, each of the two loudspeakers is respectively disposed at a corresponding one of the two side areas, and the weighted portion is disposed at the central area.

Furthermore, the weighted portion further extends to the two side areas.

Furthermore, the at least one loudspeaker is at least partially overlapped with the weighted portion along a thickness direction of the covering portion; or, the at least one loudspeaker is offset from the weighted portion along the thickness direction of the covering portion.

Furthermore, the covering portion is made of a flexible material, and the weighted portion is bendable.

Furthermore, the covering portion is arc-shaped along an arrangement direction of the central area and the two side areas.

Furthermore, each of the two side areas is bendably connected to the central area, and the two side areas are symmetrically disposed at two sides of the central area.

Furthermore, the central area defines a first accommodating space, each of the two side areas defines a second accommodating space, the first accommodating space is configured to accommodate the weighted portion, and each second accommodating space is configured to accommodate a corresponding one of the two loudspeakers.

Furthermore, the eye mask further includes a controller, the controller is disposed in an accommodating space of the mask body, and the controller is electrically connected to the at least one loudspeaker.

Furthermore, the controller includes at least one button, at least one mark portion is disposed on an outer surface of the mask body, and the at least one button is disposed corresponding to the at least one mark portion.

Furthermore, the eye mask further includes a cable, the cable is connected to the controller, and the cable is partially exposed out of the mask body for being electrically connected to an external device.

Furthermore, the mask body further defines an access opening, the access opening is communicated with the accommodating space, and the controller and the weighted portion are insertable into or removable from the accommodating space through the access opening.

Furthermore, the eye mask further includes a zipper, the zipper is disposed at the access opening for opening or closing the access opening.

Furthermore, the connecting portion includes a first connecting portion and a second connecting portion, the first connecting portion and the second connecting portion are respectively connected to the two sides of the covering portion, and the first connecting portion and the second connecting portion are detachably connected.

Furthermore, the first connecting portion defines a mounting hole, a first end of the second connecting portion is connected to the covering portion, a second end of the second connecting portion includes a hooking portion, the hooking portion is configured to mount to the mounting hole or separate from the mounting hole, a length of the second connecting portion between the covering portion and the first connecting portion is adjustable, and the second connecting portion is elastic.

Furthermore, the weighted portion includes weight reducing zones corresponding to the eyes of the human body, the weighted portion further includes a weighted zone surrounding the weight reducing zones, and at least one weighted block is disposed in the weighted zone.

Furthermore, each of the weight reducing zones is an aperture; or, a mass of each of the weight reducing zones is less than a mass of the weighted zone.

Furthermore, the weighted portion includes a textile component and weighted blocks, the textile component defines first accommodating cavities and second accommodating cavities. The first accommodating cavities are configured to align with the eyes of the human body, none of the weighted blocks is disposed in the first accommodating cavities. The second accommodating cavities are configured to offset from the eyes of the human body, each of the accommodating cavities accommodates a corresponding one of the weighted blocks.

Furthermore, the at least one weighted block includes at least one of glass beads and stones.

According to the present disclosure, the mask body is worn over the eyes of the human body, incorporates the weighted portion to form a gravity-enhanced eye mask. Upon wearing, the weighted portion exerts gentle pressure around an ocular area of the human body, ensuring superior conformity to facial contours of the human body, so as to effectively prevent light leakage from edges of the eye mask provided by the present disclosure, thereby achieving enhanced light-blocking performance. Compared to conventional eye masks, the eye mask provided by the present disclosure not only excels in light-blocking performance but also uses the gentle pressure exerted by the weighted portion to stimulate localized blood circulation around the eyes. This helps mitigate ocular fatigue and further reduces appearance of dark circles. Furthermore, proper pressure not only alleviates tension in periorbital neural network but also induces neurological relaxation, thereby reducing psychological stress and facilitating enhanced user tranquility to further improve sleep quality. Furthermore, the eye mask further includes the at least one loudspeaker disposed offset from the eyes of the human body, avoiding direct pressure on the eyes of the human body, so as to ensure wearing comfort while preserving audio playback functionality. The at least one loudspeaker is configured to reproduce soothing music, white noise, or other audio content, thereby promoting user relaxation and further improving sleep quality and ocular soothing effects. Moreover, the eye mask integrating the at least one loudspeaker enables discreet, personalized auditory experiences without disturbing others. Users may access audiobooks, language-learning modules, or entertainment content during rest periods, transforming fragmented downtime into productive or recreational opportunities. The eye mask is further capable of communicating with mobile devices, allowing the users not only to make and receive phone calls but also to remotely control audio playback, adjust volume, or select playlist. In this way, convenience and personalization of the eye mask are significantly enhanced. The eye mask integrating the at least one loudspeaker not only enhances functionality but also delivers a more comfortable, convenient, and personalized user experience. The present disclosure transforms the eye mask from a conventional light-blocking tool into a multifunctional sleep and relaxation aid, creating a multisensory soothing environment. The eye mask provided by the present disclosure is adaptable to sleep scenarios, daily relaxation, learning, and entertainment applications, which effectively addressing pursuit of modern users for a health-conscious lifestyle.

BRIEF DESCRIPTION OF DRAWINGS

In order to more clearly illustrate technical solutions in embodiments of the present disclosure, accompanying drawings required in description of the embodiments are briefly described below, and obviously, the accompanying drawings in the following description are merely some embodiments of the present disclosure, and for those who skilled in the art, other drawings may be obtained according to structures shown in these drawings without creative efforts

Figure 1:
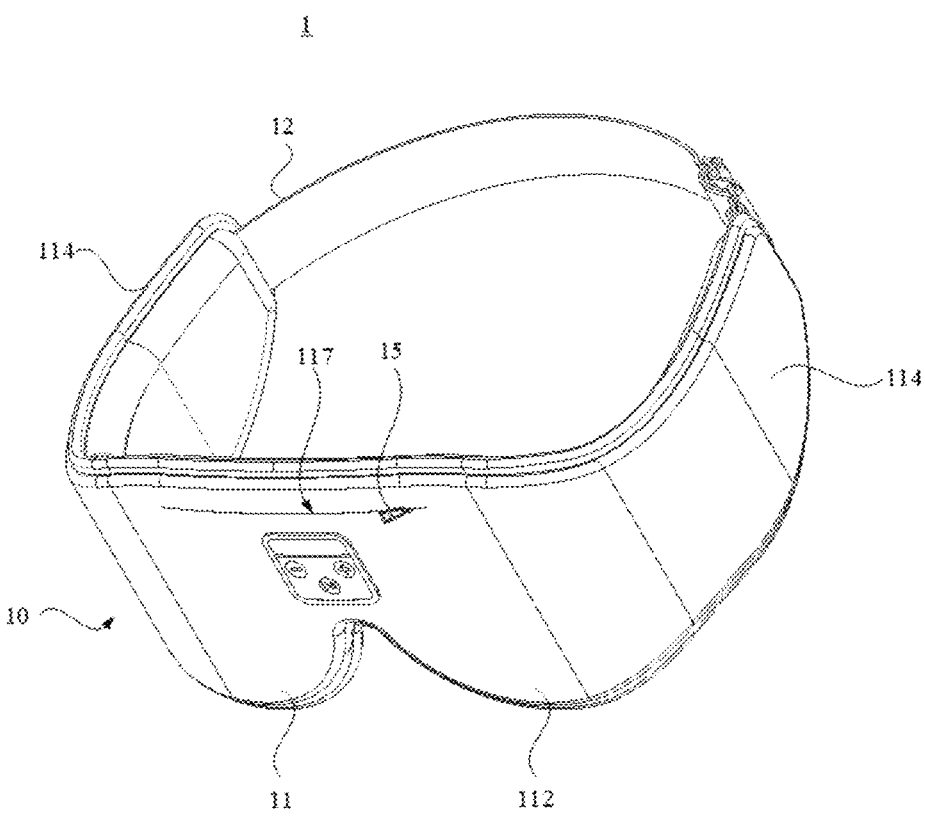
FIG. 1 is a structural schematic diagram of an eye mask according to one embodiment of the present disclosure.

Reference numerals in the drawings: 1. eye mask; 10. mask body; 11. covering portion; 111. accommodating space; 112. central area; 113. first accommodating space; 114. side area; 115. second accommodating space; 116. mark portion; 117. access opening; 12. connecting portion; 122. first connecting portion; 123. mounting hole; 124. second connecting portion; 125. hooking portion; 13. weighted portion; 131. weight reducing zone; 132. weighted zone; 14. controller; 142. button; 15. zipper; 16. cable; 20. loudspeaker.

DETAILED DESCRIPTION OF EMBODIMENTS

The following clearly and completely describes technical solutions in embodiments of the present disclosure with reference to accompanying drawings in the embodiments of the present disclosure, obviously, the described embodiments are only a part but not all of the embodiments of the present disclosure. All other embodiments obtained by those who skilled in the art based on the embodiments of the present disclosure without creative efforts shall fall within a protection scope of the present disclosure. In addition, it should be understood that specific implementations described herein are only used to illustrate and explain the present disclosure, and are not intended to limit the present disclosure.

Figure 2A:
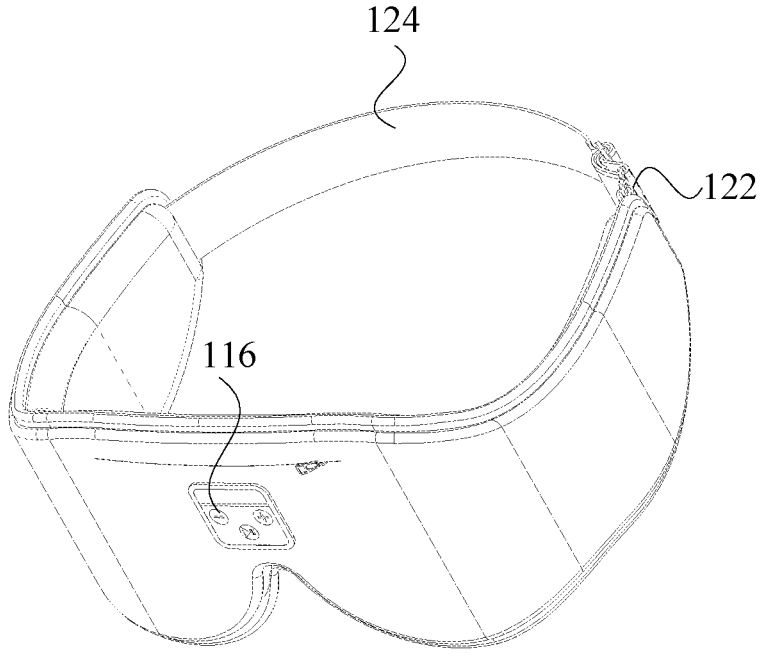
FIG. 2A is a partial structural schematic diagram of the eye mask shown in FIG. 1 when disassembled.
Figure 2B:
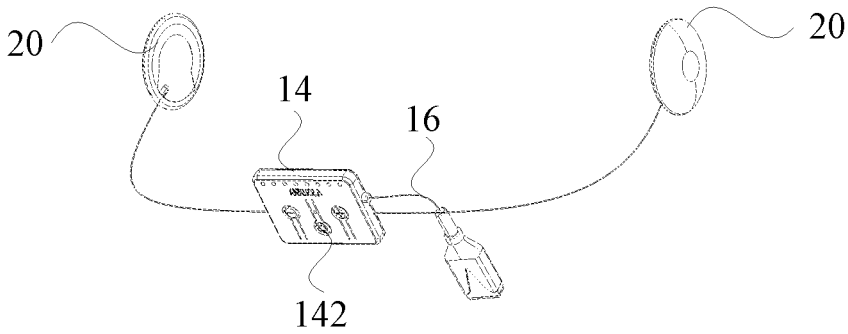
FIG. 2B is another partial structural schematic diagram of the eye mask shown in FIG. 1 when disassembled.
Figure 2C:
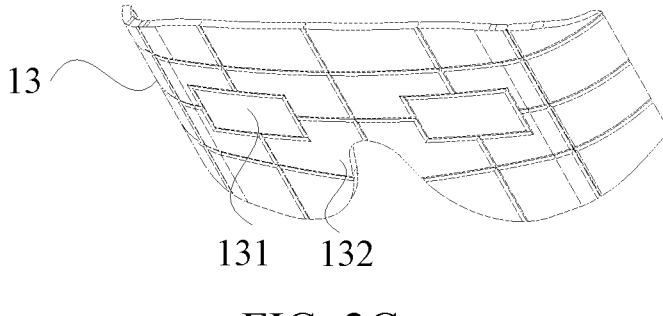
FIG. 2C is further another partial structural schematic diagram of the eye mask shown in FIG. 1 when disassembled.

Please refer to FIGS. 1-2C, FIG. 1 is a structural schematic diagram of an eye mask according to one embodiment of the present disclosure, and FIGS. 2A-2C illustrate an exploded schematic diagram of the eye mask shown in FIG. 1. The embodiments of the present disclosure provide the eye mask 1, including a mask body 10 and at least one loudspeaker 20. The mask body is configured to be worn on a human body and cover eyes of the human body, and a weighted portion 13 is disposed in the mask body 10. The at least one loudspeaker 20 is disposed in the mask body 10 and is configured to offset from the eyes of the human body.

Specifically, the mask body 10 is a main structure of the eye mask 1, the mask body 10 is worn over the eyes of the human body, incorporates the weighted portion 13 to form a gravity-enhanced eye mask. Upon wearing, the weighted portion 13 exerts gentle pressure around an ocular area of the human body, ensuring superior conformity to facial contours of the human body, so as to effectively prevent light leakage from edges of the eye mask 1 provided by the present disclosure, thereby achieving enhanced light-blocking performance. Compared to conventional eye masks, the eye mask 1 provided by the present disclosure not only excels in light-blocking performance but also uses the gentle pressure exerted by the weighted portion 13 to stimulate localized blood circulation around the eyes. This helps mitigate ocular fatigue and further reduces appearance of dark circles. Furthermore, proper pressure not only alleviates tension in periorbital neural network but also induces neurological relaxation, thereby reducing psychological stress and facilitating enhanced user tranquility to further improve sleep quality.

It should be noted that although the weighted portion 13 has a specific mass, the exerted pressure is not directly applied to eyeballs of the human body. Instead, due to scientific weight distribution and structural design, the pressure is primarily exerted on periorbital dermal and muscular tissues. Such configuration enables the eyeballs of the human body to experience a near-zero compressive sensation while maintaining optimal comfort. Moreover, the mass of the weighted portion 13 is precisely calibrated within an ergonomically safe threshold ensuring no ocular discomfort and providing users with gentle pressure that combines comfort with safety.

The eye mask 1 of the embodiments of the present disclosure further includes the at least one loudspeaker 20 disposed offset from the eyes of the human body. Such design avoids interference from both the at least one loudspeaker 20 and the weighted portion 13 with the eyes, ensuring wearing comfort while preserving audio playback functionality. The at least one loudspeaker 20 is configured to reproduce soothing music or other audio content, thereby promoting user relaxation and further improving sleep quality and ocular soothing effects. Moreover, the eye mask 1 integrating the at least one loudspeaker 20 enables discreet, personalized auditory experiences without disturbing others. Users may access audiobooks, language-learning modules, or entertainment content during rest periods, transforming fragmented downtime into productive or recreational opportunities. The eye mask 1 is further capable of communicating with mobile devices, allowing the users not only to make and receive phone calls but also to remotely control audio playback, adjust volume, or select playlist. In this way, convenience and personalization of the eye mask 1 are significantly enhanced. The eye mask 1 integrating the weighted portion 13 and the at least one loudspeaker 20 not only enhances functionality but also delivers a more comfortable, convenient, and personalized user experience. The present disclosure transforms the eye mask 1 from a conventional light-blocking tool into a multifunctional sleep and relaxation aid by incorporating both physical soothing mechanisms and audio playback functionality, creating a multisensory soothing environment. The eye mask 1 provided by the present disclosure is adaptable to sleep scenarios, daily relaxation, learning, and entertainment applications, which effectively addressing pursuit of modern users for a health-conscious lifestyle.

Figures 3, 4:
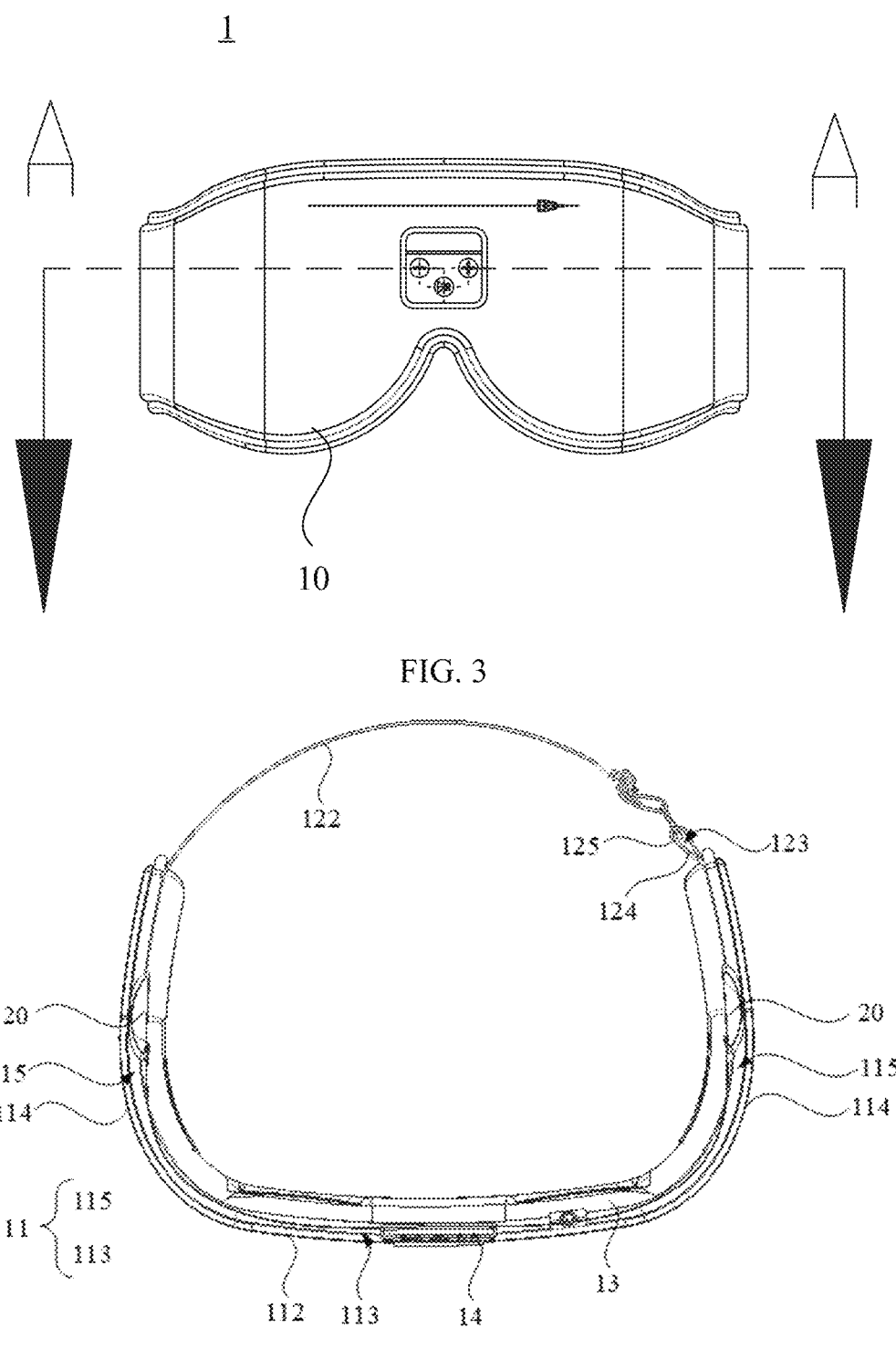
FIG. 3 is another schematic diagram of the eye mask shown in FIG. 1.
FIG. 4 is a cross-sectional schematic diagram of the eye mask shown in FIG. 3, taken long the line A-A.

Please refer to FIGS. 3-4, FIG. 3 is another schematic diagram of the eye mask 1 shown in FIG. 1, and FIG. 4 is a cross-sectional schematic diagram of the eye mask 1 shown in FIG. 3, taken long the line A-A. In some embodiments, the mask body 10 includes a covering portion 11 and a connecting portion 12, the covering portion 11 defines an accommodating space 111, the weighted portion 13 and the at least one loudspeaker 20 are disposed in the accommodating space 111, the connecting portion 12 is connected to two sides of the covering portion 11 and cooperates with the covering portion 11 to be worn on the human body.

The covering portion 11 covers the eyes of the human body, the covering portion 11 defines the accommodating space 111 for mounting the weighted portion 13 and the at least one loudspeaker 20, and integration of the weighted portion 13 and the at least one loudspeaker 20 increases functions of physical soothing and audio assistance on a basis of providing a conventional light-blocking function, thereby improving functionality of the eye mask 1. The connecting portion 12 is connected to the two sides of the covering portion 11, and is configured to fix the eye mask 1 to a head portion of the human body to ensure wearing stability and comfort.

In some embodiments, the covering portion 11 includes a central area 112 and two side areas 114, the two side areas 114 are configured to respectively cover different ears of the human body, and the central area 112 is disposed between the two side areas 114. Two loudspeakers 20 are provided, each of the two loudspeakers 20 is respectively disposed at a corresponding one of the two side areas 114, and the weighted portion 13 is disposed at the central area 112.

In the embodiments, the central area 112 of the covering portion 11 is mainly configured to cover eye portions of the eyes of the human body to provide a light-blocking and comfortable environment, meanwhile, the weighted portion 13 is disposed in the central area 112, so that the gentle pressure is exerted for the eyes, the localized blood circulation around the eyes is stimulated, and the ocular fatigue mitigated. The two side areas 114 are configured to respectively cover left and right ears of the human body, which not only enhances fit and a light blocking range of the eye mask 1 but also effectively isolates external noise, thereby further improving sleep experience of the users.

Moreover, the eye mask 1 includes the two loudspeakers 20, the two loudspeakers 20 are respectively disposed in the two side areas 114 in alignment with ear positions on left and right sides of the users, so that the audio content is directly transmitted to ears of the users to provide a clearer and three-dimensional auditory experience. Meanwhile, the two loudspeakers 20 are offset from the eyes of the human body to avoid direct pressure on the eyes, thereby ensuring wearing comfort. In the embodiments, the two loudspeakers 20 and the weighted portion 13 are respectively disposed in the two side areas 114 and the central area 112, an internal space of the covering portion 11 is reasonably utilized, and mutual interference between components is also avoided. It should be noted that, in other embodiments, the eye mask 1 includes other numbers of loudspeakers 20 as required, which is not limited herein.

In some embodiments, the weighted portion 13 is not only be disposed in the central area 112 but may also extend to the two side areas 114. Through extending the weighted portion 13 to the two side areas 114, so that the gentle pressure exerted by the weighted portion 13 is more uniformly distributed around the eyes, thereby enhancing fit and stability of the eye mask 1 and further improving the wearing comfort. It should be noted that whether the weighted portion 13 extends to the two side areas 114 is selected according to user requirements, the weighted portion 13 extends to the two side areas 114 or does not extend to the two side areas, thereby providing more diversified options for the users and meeting personalized requirements of different users.

In some embodiments, the at least one loudspeaker 20 is offset from the weighted portion 13 along a thickness direction of the covering portion 11; or, the at least one loudspeaker 20 is at least partially overlapped with the weighted portion 13 along the thickness direction of the covering portion 11.

In the covering portion 11, arrangement of the at least one loudspeaker 20 and the weighted portion 13 is flexibly adjusted according to specific requirements. The at least one loudspeaker 20 is offset from the weighted portion 13 along the thickness direction of the covering portion 11, such arrangement avoids mutual interference on functions and further ensures independence of the exerted pressure sense and sound quality. In some other examples, the at least one loudspeaker 20 is at least partially overlapped with the weighted portion 13 along the thickness direction of the covering portion 11, such arrangement helps to optimize space utilization, enabling a more compact structure of the eye mask 1. For example, when the weighted portion 13 does not extend to the two side areas 114, the at least one loudspeaker 20 is offset from the weighted portion 13 to ensure that the audio is clearly played. For another example, the weighted portion 13 extends to the two side areas 114, the at least one loudspeaker 20 is at least partially overlapped with the weighted portion 13, so that internal space of the covering portion 11 is reasonably utilized. In the embodiments, the arrangement of the at least one loudspeaker 20 and the weighted portion 13 is flexibly adjusted to meet use requirements in different scenarios and provide diversified selections for the users.

In some embodiments, the covering portion 11 is made of a flexible material, and the weighted portion 13 is bendable.

In the embodiments, the mask body 10 is made of flexible material, such as silica gel, memory foam, elastic fabric, etc. The covering portion 11 made of the flexible material is in close fit with human eye contours, which reduces the light leakage from the edges of the eye mask 1 even when the users lie on their sides, meanwhile, a comfortable wearing experience is further provided and discomfort possibly caused by a hard structure is reduced, the flexible material is suitable for long-term wearing of the eye mask 1. Furthermore, the weighted portion 13 of the mask body 10 is bendable, so as to adapt to facial shapes of different users, to better fit facial areas surrounding the eyes, in this way, the gentle pressure is generated, the localized blood circulation around the eyes is stimulated, the ocular fatigue is mitigated, and the wearing stability and comfort is further enhanced.

In some embodiments, the covering portion 11 is arc-shaped along an arrangement direction of the central area 112 and the two side areas 114.

For example, in the embodiments, the covering portion 11 is made of a relatively hard material, and the covering portion 11 is arc-shaped, in this way, the covering portion 11 maintains stability of an arc shape thereof to better fit the facial contours of the human body, and provides reliable light-blocking performance and gentle pressure.

In some embodiments, each of the two side areas 114 is bendably connected to the central area 112, and the two side areas 114 are symmetrically disposed at two sides of the central area 112.

In the embodiments, the central area 112 is in close fit with the eye portions of the eyes of the human body to provide the gentle pressure and the light-blocking performance, and the two side areas 114 are bent and extended from the two sides of the central area 112 to form a symmetrical arc shape for covering the left and right ears of the human body, so that the covering portion 11 is arc-shaped to ensure the wearing stability and comfort.

In some embodiments, the two loudspeakers 20 are provided. The central area 112 defines a first accommodating space 113, each of the two side areas 114 defines a second accommodating space 115, the first accommodating space 113 is configured to accommodate the weighted portion 13, and each second accommodating space 115 is configured to accommodate a corresponding one of the two loudspeakers 20.

In the embodiments, the first accommodating space 113 accommodates the weighted portion 13, and each second accommodating space 115 accommodates the corresponding one of the two loudspeakers 20. Such arrangement enables the weighted portion 13 and the two loudspeakers 20 to be spatially separated from each other, and the weighted portion 13 and the two speakers 20 are respectively disposed in different accommodating spaces, ensuring that the weighted portion 13 and the speaker 20 do not interfere with each other. Specifically, the weighted portion 13 is accommodated in the first accommodating space 113 of the central area 112, so as to exert the gentle pressure for the eyes of the human body, in this way, the localized blood circulation around the eyes is stimulated, and the ocular fatigue is mitigated. Each of the two loudspeakers is accommodated in a corresponding second accommodating space 115, which is close to a corresponding ear of the users, so as to provide a clear and three-dimensional auditory experience.

In some embodiments, the eye mask 1 further includes a controller 14, the controller 14 is disposed in an accommodating space 111 of the mask body 10, and the controller 14 is electrically connected to the at least one loudspeaker 20.

In the embodiments, the accommodating space 111 in the mask body 10 is configured to accommodate not only the weighted portion 13 but also the controller. The controller 14 is configured to adjust a volume of the at least one loudspeaker 20, switch the playlist or control a playback mode, etc., so as to provide a more convenient and personalized auditory experience for the users. By accommodating the controller 14 in the accommodating space 111, an internal space of the accommodating space 111 can be fully utilized, thereby ensuring a compact structure of the eye mask 1.

For example, the two loudspeakers 20 are provided, the controller 14 is disposed in the first accommodating space 113 of the central area 112, the controller 14 is electrically connected to the two loudspeakers 20 at both sides through a connecting wire, and the connecting wire passes between the first accommodating space 113 and each second accommodating space 115, which not only implements effective control of the two loudspeakers 20 by the controller 14, ensures stable transmission of audio signals, but also improves overall esthetic appeal and security of the eye mask 1.

In some embodiments, the controller 14 includes at least one button 142, at least one mark portion 116 is disposed on an outer surface of the mask body 10, and the at least one button 142 is disposed corresponding to the at least one mark portion 116.

In the embodiments, the controller 14 is disposed in the accommodating space 111 of the mask body 10 and includes the at least one button 142 for directly controlling the at least one loudspeaker 20, such as volume adjustment, playlist switching, or playback mode controlling. In order to facilitate the users to operate when wearing the eye mask 1, the at least one mark portion 116 is disposed on the outer surface of the mask body 10, and the at least one button 142 is disposed corresponding to the at least one mark portion 116. The at least one mark portion 116 is disposed on the outer surface of the mask body 10 by printing, sewing, gluing, etc. For example, the controller 14 is disposed in the central area 112 of the mask body 10, and the at least one mark portion 116 is located at a relatively middle portion of a front surface of the eye mask 1, which is clear and easy to touch and recognize, even in a pitch-black or dark environment, the users may easily find a corresponding position of the at least one button 142 through the at least one mark portion 116, thereby achieving a convenient operation experience. Such design not only improves operation convenience of the users during using the eye mask 1, but also ensures overall attractiveness and simplicity of the eye mask 1, so as to provide the users with a comfortable and convenient experience while enjoying the audio content.

In some embodiments, the eye mask 1 further includes a cable 16, the cable 16 is connected to the controller 14, and the cable 16 is partially exposed out of the mask body 10 for being electrically connected to an external device.

In the embodiments, the cable 16 connected to the controller 14 is partially exposed out of the mask body 10 for being electrically connected to the external device, so that the controller 14 not only controls the at least one loudspeaker 20 inside the eye mask 1 but also is easy to be electrically connected to the external device, such as a mobile phone, a tablet, or an audio player, etc., through the cable 16, which further expands functions of the eye mask 1, and enhances applicability of the eye mask 1 in different scenarios.

In some embodiments, the cable 16 is connected to a power supply to power the controller 14 and the at least one loudspeaker 2.

In the embodiments, the eye mask 1 is connected to an external power supply, stable power support is provided for the controller 14 and the at least one loudspeaker 20 through the external power supply, which ensures that an audio function of the eye mask 1 and a function of the controller 14 are always kept running, and practicability of the eye mask 1 is improved.

In some embodiments, the cable 16 is connected to an audio source device for providing audio signals to the controller 14 and the at least one loudspeaker 20.

In the embodiments, the cable 16 of the eye mask 1 is further connected to the audio source device for providing the audio signals. In this way, the controller 14 receives the audio signals from an external audio source device, such as the mobile phone, the tablet computer, or the audio player, through the cable 16 and transmits the audio signals to the at least one loudspeaker 20 for playing, so that the users may select preferred audio content, such as music, white noise, the audiobooks, etc., to enjoy a personalized auditory experience. In addition, through cooperation of the at least one loudspeaker 20 and the controller 14, when the users wear the eye mask 1, the users can also make phone calls through the at least one loudspeaker 20 without removing the eye mask 1 or additionally using an earphone, such design not only meets audio requirements of the users during relaxation or sleep but also provides a convenient call function, thereby further improving the practicability of the eye mask 1.

It should be noted that, in order to provide more flexibility and portability, the eye mask 1 further includes a built-in battery. The users may select to connect the eye mask 1 to the external power supply or use the built-in battery as required. In some embodiments, the built-in battery is a rechargeable battery, and the built-in battery is charged through the external power supply and a corresponding cable. In some other embodiments, the eye mask 1 supports wireless charging and the built-in battery wirelessly charged, there is no need to provide the corresponding cable for charging, so that the eye mask 1 is more flexible in use. In addition, in some embodiments, the eye mask 1 further receives the audio signals through a wireless technology, such as Bluetooth, thereby further reducing constraint of the cable 16, and the users may feel freer and more convenient during use.

In some embodiments, the mask body 10 further defines an access opening 117, the access opening 117 is communicated with the accommodating space 111, and the controller 14 and the weighted portion 13 are insertable into or removable from the accommodating space 111 through the access opening 117.

In the embodiments, the mask body 10 defines the access opening 117 communicated with the accommodating space 111, for example, the access opening 117 is located at the front surface of the eye mask 1 or other positions of the eye ask 1, and the controller 14, the weighted portion 13, the cable 16, etc., are insertable into or removable from the accommodating space 111 through the access opening 117. Specifically, in some embodiments, the controller 14, the weighted portion 13, and the cable 16 are completely hidden in the accommodating space 111, so that an appearance of the eye mask 1 is kept concise and integrity during use. Meanwhile, when it is necessary to operate the controller 14, replace the weighted portion 13, or connect to the external device, the controller 14, the weighted portion 13, or the cable 16 is removed from the accommodating space 111 through the access opening 117, such a flexible design not only facilitates the users to adjust configuration of the eye mask 1 according to requirements but also improves the practicability and convenience of the eye mask 1. For example, the access opening 117 communicated with the first accommodating space 113 is defined at the central area 112, and the controller 14 and the weighted portion 13 are insertable into or removable from the first accommodating space 113 through the access opening 117.

In some embodiments, the eye mask 1 further includes a zipper 15, the zipper 15 is disposed at the access opening 117 for opening or closing the access opening 117.

In the embodiments, the eye mask 1 further includes the zipper 15 for controlling opening and closing of the access opening 117. Such zipper design enables the users to conveniently open the access opening 117 to place the controller 14, the weighted portion 13, and the cable 16 into or out of the first accommodating space 113. When the controller 14, the weighted portion 13, and the cable 16 need to be hidden, the zipper 15 completely closes the access opening 117, ensuring that the controller 14 and the weighted portion 13 are safely accommodated in the first accommodating space 113, while maintaining cleanliness and esthetic appeal of the appearance of the eye mask 1. Moreover, such design of the access opening 117 with the zipper 15 also enhances sealing performance of the eye mask 1, and prevents dust or other debris from entering the accommodating space 111, thereby prolonging a service life of the controller 14, the weighted portion 13, and the cable 16 housed inside the eye mask and maintaining performance thereof.

In some embodiments, the connecting portion 12 is elastic, so that the eye mask 1 better fits head contours of different users during wearing, and tightness thereof is automatically adjusted according to head types of the users, thereby ensuring wearing comfort and stability. Moreover, the connecting portion 12 being elastic not only facilitates quick wearing and taking off of the eye mask 1 by the users but also effectively reduces discomfort possibly caused by long-term wearing, thereby further improving user experience.

In some embodiments, the connecting portion 12 includes a first connecting portion 122 and a second connecting portion 124, the first connecting portion 122 and the second connecting portion 124 are respectively connected to the two sides of the covering portion 11, and the first connecting portion 122 and the second connecting portion 124 are detachably connected.

In the embodiments, the connecting portion 12 is composed of the first connecting portion 122 and the second connecting portion 124, and the first connecting portion 122 and the second connecting portion 124 are detachably connected, which is convenient for the users to disconnect the eye mask 1 to take off the eye mask from a user head, or establish a connection, so as to wear the eye mask 1 and provide a convenient wearing experience. It should be noted that, in some embodiments, the connecting portion 12 is integrated, is worn by elastic stretching, and is also automatically adapt to sizes of head types of different users without additional adjustment or disassembly operations. In the embodiments, a design of the connecting portion 12 is selected according to different usage requirements, either as a detachable two-piece structure or as an integrated elastic structure, thereby providing the users with diversified options.

In some embodiments, the first connecting portion 122 defines a mounting hole 123, a first end of the second connecting portion 124 is connected to the covering portion 11, a second end of the second connecting portion 124 includes a hooking portion 125, the hooking portion 125 is configured to mount to the mounting hole 123 or separate from the mounting hole 123, a length of the second connecting portion 124 between the covering portion 11 and the first connecting portion 122 is adjustable, and the second connecting portion 124 is elastic.

In the embodiments, the first connecting portion 122 defines the mounting hole 123, the first end of the second connecting portion 124 is connected to the covering portion 11 and the second end of the second connecting portion 124 includes a hooking portion 125 to implement connection and fixation. When the length of the eye mask 1 needs to be adjusted, the users separate the hooking portion 125 from the mounting hole 123, and then re-mount the hooking portion 125 into the mounting hole 123 after adjusting a length of the second connecting portion 124, so that the length of the second connecting portion 124 between the covering portion 11 and the first connecting portion 122 is easily adjusted according to the head types or wearing requirements of different users to adjust an overall length of the connecting portion 12, thereby flexibly adjusting the tightness of the eye mask 1 and achieving a more comfortable and more fit wearing effect. In addition, the second connecting portion 124 has elasticity, which further enhances adaptability and comfort of the eye mask 1, and such elastic design enables the second connecting portion 124 to automatically extend and retract within a certain range, thereby better fitting the head contours of different users. Even if the eye mask 1 faces the head types of different users, the eye mask 1 still maintains good fit and stability, and meanwhile, discomfort possibly caused by long-term wearing is reduced.

In some embodiments, the weighted portion 13 includes weight reducing zones 131 corresponding to the eyes of the human body, the weighted portion 13 further includes a weighted zone 132 surrounding the weight reducing zones 131, and at least one weighted block is disposed in the weighted zone 132.

By providing the weight reducing zones 131 corresponding to the eyes of the human body, a weight of areas corresponding to the eyes of the human body, namely the weight reducing zones 131, is effectively reduced, excessive pressure or burden on the eyes of the human body is avoided, the wearing comfort is improved, and the fatigue feeling caused by long-term wearing is reduced. The at least one weighted block is disposed in the weighted zone 132 surrounding the weight reducing zones 131, the weighted zone 132 surrounds the weight reducing zones 131, which is also understood as that the weighted zone 132 is disposed surrounding the eyes of the human body, so that micrograv- ity is applied to the facial areas surrounding the eyes to stimulate nerves and blood vessels surrounding the eyes to stimulate the blood circulation, thereby helping to relax the human body, relieve pressure, and improve sleep quality, and does not directly apply gravity to the eyes, so that discomfort is not caused to the eyeballs of the human body. Such design also enables the eye mask to be more fit to the human eye contours during wearing, and does not cause excessive compression on the eyeballs of the human body.

A material of the at least one weighted block may be flexibly selected according to design requirements of the eye mask 1 and personalized usage habits of different user. In some embodiments, the at least one weighted block includes at least one of glass beads and stones. The glass beads each has a smooth, rounded surface and a moderate weight, providing a uniform and comfortable pressure on the eyes, which helps to mitigate the ocular fatigue. In contrast, the stones offer a reliable pressure effect due to natural texture and stable weight, effectively relaxing the eye muscles.

It should be noted that, in addition to the glass beads and the stones, in some embodiments, the at least one weighted block is made from other materials, such as metal particles, high-density plastic, etc. By offering a variety of weighting materials, the eye mask 1 better meets the personalized requirements of different users and enhances the wearing experience. For example, the weighted portion 13 is remov- able from the accommodating space 111, allowing the users to conveniently replace the weighted portion 13 with dif- ferent materials based on their own requirements or prefer- ences, thereby increasing flexibility of the eye mask 1.

In some embodiments, each of the weight reducing zones 131 is an aperture. The weighted portion 13 defines each aperture corresponding to a corresponding eye of the human body, thereby exerting minimal pressure on the eyeball, achieving localized weight reduction while preserving an overall structure and function of the eye mask 1. Such design further reduces a weight of the weighted portion 13, increases breathability of the eye mask 1, and minimizes stuffy feeling during wearing, so as to further enhance the wearing experience.

In some embodiments, a mass of the weight reducing zones 131 is less than a mass of the weighted zone 132. The weight reducing zones 131 are not provided with corre- sponding aperture but each is filled with other structures, such as a textile component, so that integrity of the weight reducing zones 131 is maintained, and the weight of each of the weight reducing zones 131 is reduced, thereby reducing compression on the eyeballs of the human body. In some examples, the weight reducing zones 131 are not provided with the at least one weighted block. In some other examples, the weight reducing zones 131 are provided with a small number of weighted blocks to provide proper pressure for the eyeballs of the human body to meet require- ments of different customers.

In some embodiments, the weighted portion 13 includes a textile component and weighted blocks, the textile com- ponent defines first accommodating cavities and second accommodating cavities. The first accommodating cavities are configured to align with the eyes of the human body, none of the weighted blocks is disposed in the first accom- modating cavities. The second accommodating cavities are configured to offset from the eyes of the human body, each of the accommodating cavities accommodates a correspond- ing one of the weighted blocks.

The textile component defines the first accommodating cavities and the second accommodating cavities. The first accommodating cavities are configured to align with the eyes of the human body, none of the weighted blocks is disposed in the first accommodating cavities, so that a weight reduction effect is achieved, and the pressure on the eyeballs is reduced. The second accommodating cavities are configured to offset from the eyes of the human body, each of the accommodating cavities accommodates the corre- sponding one of the weighted blocks for applying micro- gravity to stimulate the blood circulation and relaxation surrounding the eyes of the human body. Weight reduction of the first accommodating cavities and counterweight of the second accommodating cavities cooperates to achieve an overall weight balance of the eye mask 1, and the eye mask 1 does not shift out of place due to uneven weight distri- bution during wearing. Such multi-cavity design of the textile component not only optimizes weight distribution, but also enhances overall structural stability of the eye mask 1. Softness of the textile component enables the eye mask 1 to better fit the facial contours of the human body, and reduces shaking during wearing. By reasonably distributing the weighted blocks, needs for unnecessary materials are reduced, a production cost is reduced, and durability of the eye mask 1 is improved.

A number of the first accommodating cavities corresponding to the eyes of the human body is selected as required. For example, one first accommodating cavity is provided corresponding to one eye. For another example, a plurality of first accommodating cavities are provided corresponding to the one eye.

It may be understood that a number and a distribution of the second accommodating cavities are adjusted as required, and a number and a mass of the weighted blocks in each of the second accommodating cavities are adjusted as required. For example, the weight distribution of the eye mask 1 is changed by increasing or decreasing the number and the mass of the weighted blocks to adapt to different usage scenarios. In some examples, other materials are added in the first accommodating cavities and the second accommodating cavities as required. For example, a heating material is added into the first accommodating cavities, and an aromatherapy material is added into a part of the second accommodating cavities, thereby further improving the user experience.

The eye mask in the embodiments of the present disclosure is described in detail above, and specific examples are used herein to describe principles and the embodiments of the present disclosure, and description of the above embodiments is only used to help understand a method of the present disclosure and a core idea thereof; meanwhile, for those who skilled in the art, according to the idea of the present disclosure, there may be changes in specific embodiments and application ranges. In summary, a content of the present specification should not be construed as limiting the present disclosure.

What is claimed is:

1. An eye mask, comprising:
a mask body; and
at least one loudspeaker;
wherein the mask body is configured to be worn on a human body and cover eyes of the human body, and a weighted portion is disposed in the mask body;
wherein the at least one loudspeaker is disposed in the mask body and is configured to offset from the eyes of the human body;
wherein the mask body comprises a covering piece and a connecting piece, the covering piece defines an accommodating space, the weighted portion and the at least one loudspeaker are disposed in the accommodating space, the connecting piece is connected to two sides of the covering piece and cooperates with the covering piece to be worn on the human body;
the covering piece comprises a central portion and two side portions, the two side portions are configured to respectively cover different ears of the human body, and the central portion is disposed between the two side portions; wherein the central portion has a substantially flat shape, and wherein each of the two side portions is bendably connected to the centra portion through a substantially rounded corner; and
wherein there are disposed two loudspeakers, wherein each of the two loudspeakers is disposed at a corresponding one of the two side portions, and the weighted portion is disposed at the central portion;
wherein the weighted portion further extends past the rounded corner at each side to the two side portions, wherein the weighted portion comprises a substantially flat section corresponding to the central portion of the covering piece and two side sections respectively corresponding to the two side portions of the covering piece;
wherein the at least one loudspeaker at least partially overlaps the weighted portion along a thickness direction of the covering piece;
wherein the eye mask further comprises a controller disposed in an accommodating space of the mask body and electrically connected to the at least one loudspeaker; wherein the controller comprises at least one button configured to be pressed in order to trigger an electrical signal for directly controlling the at least one loudspeaker, and wherein there is disposed at least one mark portion on an outer surface of the mask body, each of the at least one mark being an identifier configured to be touched for tactilely locating a corresponding button; wherein the at least one button is disposed corresponding to the at least one mark portion.

2. The eye mask according to claim 1, wherein the covering piece is made of a flexible material, and the weighted portion is bendable to conform to facial contours of different users.

3. The eye mask according to claim 1, wherein the covering piece is arc-shaped along an arrangement direction of the central portion and the two side portions.

4. The eye mask according to claim 3, wherein the two side portions are symmetrically disposed at two sides of the central portion.

5. The eye mask according to claim 1, wherein the central portion defines a first accommodating space, each of the two side portions defines a second accommodating space, wherein the first accommodating space is configured to accommodate the weighted portion, and each second accommodating space is configured to accommodate a corresponding one of the two loudspeakers.

6. The eye mask according to claim 1, wherein the eye mask further comprises a cable, the cable is connected to the controller, and the cable is partially exposed out of the mask body for being electrically connected to an external device.

7. The eye mask according to claim 1, wherein the mask body further defines an access opening, the access opening is communicated with the accommodating space, and the controller and the weighted portion are insertable into or removable from the accommodating space through the access opening.

8. The eye mask according to claim 7, wherein the eye mask further comprises a zipper, the zipper is disposed at the access opening for opening or closing the access opening.

9. The eye mask according to claim 1, wherein the connecting piece comprises a first connecting piece and a second connecting piece, the first connecting piece and the second connecting piece are respectively connected to the two sides of the covering piece, and the first connecting piece and the second connecting piece are detachably connected.

10. The eye mask according to claim 9, wherein the first connecting piece defines a mounting hole, a first end of the second connecting piece is connected to the covering piece, a second end of the second connecting piece comprises a hooking portion, the hooking portion is configured to mount to the mounting hole or separate from the mounting hole, a length of the second connecting piece between the covering piece and the first connecting piece is adjustable, and the second connecting piece is elastic.

11. The eye mask according to claim 1, wherein the weighted portion comprises weight reducing zones corresponding to the eyes of the human body, the weighted portion further comprises a weighted zone surrounding the weight reducing zones, and at least one weighted block is disposed in the weighted zone.

12. The eye mask according to claim 11, wherein each of the weight reducing zones is an aperture.

13. The eye mask according to claim 11, wherein the weighted portion comprises a textile component and weighted blocks, the textile component defines first accommodating cavities and second accommodating cavities;

the first accommodating cavities are configured to align with the eyes of the human body, none of the weighted blocks is disposed in the first accommodating cavities; and the second accommodating cavities are configured to offset from the eyes of the human body, each of the accommodating cavities accommodates a corresponding one of the weighted blocks.

14. The eye mask according to claim 11, wherein the at least one weighted block comprises at least one of glass beads and stones.

15. The eye mask according to claim 13, wherein a heating material is disposed in at least one of the first accommodating cavities, and an aromatherapy material is added into at least one of the second accommodating cavities.

16. The eye mask according to claim 1, wherein the weighted portion is removable from the accommodating space and replaceable with one made of a different material.

17. The eye mask according to claim 1, further comprising a built-in battery, the built-in battery being a rechargeable battery and is configured to be charged through an external power supply.

18. The eye mask according to claim 1, further comprising a built-in battery, the built-in battery being a rechargeable battery and is configured to be charged wirelessly through wireless charging.

19. The eye mask according to claim 1, wherein the eye mask is operative to receive audio signals wirelessly through a wireless technology.

\* \* \* \* \*